United States Patent
Chappa et al.

(10) Patent No.: US 7,348,055 B2
(45) Date of Patent: *Mar. 25, 2008

(54) REAGENT AND METHOD FOR PROVIDING COATINGS ON SURFACES

(75) Inventors: Ralph A. Chappa, Prior Lake, MN (US); Sean M. Stucke, Farmington, MN (US); Richard A. Amos, St. Anthony, MN (US); Terrence P. Everson, Eagan, MN (US); Stephen J. Chudzik, St. Paul, MN (US); Dale G. Swan, St. Louis Park, MN (US); Peter H. Duquette, Edina, MN (US)

(73) Assignee: SurModics, Inc., Eden Prairie, MN (US)

( * ) Notice: Subject to any disclaimer, the term of this patent is extended or adjusted under 35 U.S.C. 154(b) by 397 days.

This patent is subject to a terminal disclaimer.

(21) Appl. No.: 10/028,518

(22) Filed: Dec. 21, 2001

(65) Prior Publication Data

US 2003/0165613 A1 Sep. 4, 2003

(51) Int. Cl.
*B32B 27/00* (2006.01)
(52) U.S. Cl. .............. 428/319.3; 428/319.7; 522/36; 522/46; 522/47; 522/48
(58) Field of Classification Search .......... 428/318.6, 428/319.3; 522/36, 46, 47, 48
See application file for complete search history.

(56) References Cited

U.S. PATENT DOCUMENTS

| | | |
|---|---|---|
| 4,722,906 A | 2/1988 | Guire |
| 4,826,759 A | 5/1989 | Guire et al. |
| 4,973,493 A | 11/1990 | Guire |
| 4,979,959 A | 12/1990 | Guire |
| 5,002,582 A | 3/1991 | Guire et al. |
| 5,073,484 A | 12/1991 | Guire et al. |
| 5,217,492 A | 6/1993 | Guire et al. |
| 5,258,041 A | 11/1993 | Guire et al. |
| 5,263,992 A | 11/1993 | Guire |
| 5,414,075 A | 5/1995 | Swan et al. |
| 5,512,329 A | 4/1996 | Guire |
| 5,512,474 A | 4/1996 | Clapper et al. |
| 5,563,056 A | 10/1996 | Swan et al. |
| 5,637,460 A | 6/1997 | Swan et al. |
| 5,714,360 A | 2/1998 | Swan et al. |
| 5,741,551 A | 4/1998 | Guire et al. |
| 5,744,515 A | 4/1998 | Clapper |
| 5,783,502 A | 7/1998 | Swanson |
| 5,858,653 A | 1/1999 | Duran et al. |
| 5,942,555 A | 8/1999 | Swanson et al. |
| 6,007,833 A | 12/1999 | Chudzik et al. |
| 6,020,147 A | 2/2000 | Guire et al. |
| 6,077,698 A | 6/2000 | Swan et al. |
| 6,090,995 A | 7/2000 | Reich et al. |
| 6,096,369 A | 8/2000 | Anders et al. |
| 6,121,027 A | 9/2000 | Clapper et al. |
| 6,156,345 A | 12/2000 | Chudzik et al. |
| 6,214,901 B1 | 4/2001 | Chudzik et al. |
| 6,221,425 B1 | 4/2001 | Michal et al. ............. 427/2.25 |
| 6,245,089 B1 | 6/2001 | Daniel et al. |
| 6,515,039 B1 * | 2/2003 | Ulbricht et al. ............. 522/114 |
| 6,669,994 B2 * | 12/2003 | Swan et al. ................. 427/517 |
| 6,706,408 B2 * | 3/2004 | Jelle ........................... 428/447 |
| 7,087,658 B2 * | 8/2006 | Swan et al. .................... 522/36 |

FOREIGN PATENT DOCUMENTS

| | | |
|---|---|---|
| WO | 85/01852 | 4/1986 |
| WO | 87/01018 | 11/1987 |
| WO | 87/02675 | 4/1988 |
| WO | 88/04491 | 6/1989 |
| WO | PCT/US89/02914 | 1/1990 |
| WO | 88/04487 | 2/1990 |
| WO | PCT/US90/05028 | 4/1991 |
| WO | PCT/US90/06554 | 5/1991 |
| WO | PCT/US93/01248 | 8/1993 |
| WO | PCT/US93/10523 | 5/1994 |
| WO | PCT/US94/12659 | 5/1995 |
| WO | PCT/US96/07695 | 11/1996 |
| WO | PCT/US96/08797 | 12/1996 |
| WO | PCT/US96/17645 | 5/1997 |
| WO | PCT/US97/05344 | 9/1997 |

(Continued)

OTHER PUBLICATIONS

"Radical Polymerization," C.H. Bamford, pp. 940-957 in Kroschwitz, ed., *Concise Encyclopedia of Polymer Science and Engineering*, 1990.
"Plastics," pp. 462-464, in *Concise Encyclopedia of Polymer Science and Engineering*, Kroschwitz, ed., John Wiley and Sons, 1990.
"A Novel Modification of Polymer Surfaces by Photografting," Tazuke et al., pp. 217-241, in *Modification of Polymers*, ACS Symposium Series 121 American Chemical Society, 1980.

*Primary Examiner*—Hai Vo
(74) *Attorney, Agent, or Firm*—Fredrikson & Byron, P.A.

(57) ABSTRACT

A grafting reagent and related method of using the reagent to form a polymeric layer on a support surface, and particularly a porous support surface, in a manner that provides and/or preserves desired properties (such as porosity) of the surface. The reagent and method can be used to provide a thin, conformable, uniform, uncrosslinked coating having desired properties onto the surface of a preformed, and particularly a porous, polymeric substrate. The method includes the steps of a) providing a porous support surface, b) providing a nonpolymeric grafting reagent comprising a photoinitator group, c) providing one or more polymerizable monomers adapted to be contacted with the surface, in the presence of the grafting reagent, and to be polymerized upon activation of the photoinitiator; and d) applying the grafting reagent and monomer(s) to the surface in a manner, and under conditions, suitable to coat the surface with the grafting reagent and to cause the polymerization of monomers to the surface upon activation of the grafting reagent.

8 Claims, 1 Drawing Sheet

| | FOREIGN PATENT DOCUMENTS | |
|---|---|---|
| WO | PCT/US98/16605 | 2/1999 |
| WO | PCT/US98/20140 | 4/1999 |
| WO | WO99/15917 | 4/1999 |
| WO | PCT/US99/03862 | 9/1999 |
| WO | PCT/US99/05244 | 9/1999 |
| WO | PCT/US99/05245 | 9/1999 |
| WO | PCT/US99/08310 | 11/1999 |
| WO | PCT/US99/12533 | 12/1999 |
| WO | WO 200012575 A1 * | 3/2000 |
| WO | PCT/US00/00535 | 7/2000 |
| WO | PCT/US00/01944 | 8/2000 |
| WO | PCT/US99/21247 | 3/2001 |
| WO | WO 01/17575 | 3/2001 |
| WO | PCT/US00/33643 | 6/2001 |
| WO | PCT/US01/40255 | 9/2001 |

* cited by examiner

Figure 1

Friction Measurements by Vertical Pinch Method

REAGENT AND METHOD FOR PROVIDING COATINGS ON SURFACES

TECHNICAL FIELD

The present invention relates to chemical and/or physical modification of the surface properties of industrially and medically important substrates. In one such aspect, the invention relates to the modification of the surfaces of materials having small pores or apertures, such as distal protection devices for use in blood filtering. In a related aspect, the present invention relates to the modification of surface properties for such purposes as providing surfaces with desired characteristics, such as hydrophilicity and lubricity. In a particular aspect, the invention relates to such surface modification techniques as chemical derivatization and photoinitiated polymerization.

BACKGROUND OF THE INVENTION

The chemical modification of surfaces to achieve desired chemical and/or physical characteristics has been previously described. Often, the various coatings and techniques referred to above are used to coat the surfaces of materials (e.g., medical devices) intended for temporary or permanent placement in the body. In turn, the resulting coatings typically provide a desired function or feature, such as lubricity, and must do so in a manner that provides the desired combination of such other properties as hemocompatability, durability, and sterility.

A number of patents generally relate to surface modification by the use of latent reactive groups to achieve covalent coupling of agents such as biomolecules and synthetic polymers to various substrates. See, for example, Applicant's U.S. Pat. Nos. 4,722,906, 4,826,759, 4,973,493, 4,979,959, 5,002,582, 5,073,484, 5,217,492, 5,258,041, 5,263,992, 5,414,075, 5,512,329, 5,512,474, 5,563,056, 5,637,460, 5,714,360, 5,741,551, 5,744,515, 5,783,502, 5,858,653, 5,942,555, 6,007,833, 6,020,147, 6,077,698, 6,090,995, 6,121,027, 6,156,345, 6,214,901 and published PCT Application Nos. US82/06148, US87/01018, US87/02675, US88/04487, US88/04491, US89/02914, US90/05028, US90/06554, US93/01248, US93/10523, US94/12659, US96/07695, US96/08797, US96/17645, US97/05344, US98/16605, US98/20140, US99/03862, US99/05244, US99/05245, US99/08310, US99/12533, US99/21247, US00/00535, US00/01944, US00/33643, and US01/40255, (each of which is commonly owned by the assignee of the invention described herein, and the disclosure of each is incorporated herein by reference). The preferred latent reactive group is often described as a photochemically reactive functional group ("photoreactive group"). When exposed to an appropriate energy source, a latent reactive (e.g., photoreactive) group undergoes a transformation from an inactive state (i.e., ground state) to a reactive intermediate capable of forming covalent bonds with appropriate materials.

Such latent reactive groups can be used, for instance, to first derivatize a target molecule (e.g., thermochemically), in order to then photochemically attach the derivatized target molecule to a surface. Such a sequential approach is suitable in many situations, but can lack such attributes as speed, versatility, and ease of use, particularly when used with target molecules that are inherently difficult to first derivative, or need to be used under conditions that would result in loss of desirable (e.g., biological) activity.

In another approach, the surface itself can be provided (e.g., derivatized or "primed") with latent reactive groups, which can then be activated while target molecules are in sufficient proximity to become thus attached to the surface. For instance, Applicant's U.S. Pat. No. 5,414,075, describes the use of linking agents to prime a surface to provide the surface with photoactivatable groups. This patent describes a restrained, multifunctional reagent useful for priming a support surface, or for simultaneous application with a target molecule to a support.

By contrast, there appear to be relatively few examples of surface coatings that are provided by the formation of polymers in situ upon the surface, e.g., by grafting. For instance, Tazuke et al. discuss the modification of polymer surfaces by the use of a grafting technique that involves treating a base polymer (e.g., polypropylene) with a reacting solution that contains sensitizers (e.g., benzophenone) and a selected polymer to be grafted onto the base polymer. "A Novel Modification of Polymer Surfaces by Photografting," Tazuke et al., pp. 217-241, in *Modification of Polymers*, ACS Symposium Series 121 American Chemical Society, 1980. The use of polymeric photosensitizers for initiating polymerization has also been described. See, for instance, "Radical Polymerization," C. H. Bamford, pp. 940-957 in Kroschwitz, ed., *Concise Encyclopedia of Polymer Science and Engineering*, 1990.

Moreover, Applicant's own U.S. Pat. No. 5,741,551 describes the manner in which molecules of reactive chemical unit can be bonded to a surface, via the activation of latent reactive groups. In turn, a different monomer, oligomer or polymer can be covalently bound to the reactive chemical unit, and in turn, to the support surface, for instance, by means of a polymerization reaction between the two.

In a related manner, Applicant's U.S. Pat. No. 5,714,360 describes a chemical linking agent comprising a di- or higher functional photoactivatable charged compound. The linking agent has increased hydrophilic character, as compared to the reagents of the '075 patent above. Applicant's co-pending International PCT application No. PCT/US99/21247 further provides a method for the use of reagents of the type described in the '360 patent as coating agents for forming a polymeric layer on a surface by graft polymerization. In its Background section, the co-pending PCT application describes common methods of attaching a polymer to a support surface, including the attachment of a preformed polymer to a surface, and grafting a polymer to a surface.

PCT Publication No. WO 99/15917 (Baron, Novartis AG) describes a method for treating the surfaces of siloxane-containing hydrogel contact lenses. The publication describes the manner in which preformed polymers are grafted onto a surface using photo groups (such as benzophenone) as photosensitizers. In a first treatment, the surface is functionalized by dipping it in a solvent solution containing the photosensitizer. Thereafter, the functionalized surface is contacted with a solution containing macromer, which is grafted to the surface upon the application of UV light.

PCT Publication No. WO 01/17575 (STS Biopolymers, Inc.) describes a method for graft polymerization of substrate surfaces. The publication describes a method of coating a substrate, involving exposing a substrate to an initiator capable of initiating a graft polymerization reaction on the substrate, to generate reactive radical sites on the surface of the substrate; contacting the substrate with a composition comprising one or more monomers in a medium which has different hydrophilicity compared to the substrate, and grafting monomer molecules onto the substrate by forming covalent bonds between monomer molecules and the substrate at reactive radical sites on the substrate surface.

See also Anders et al., U.S. Pat. No. 6,096,369, which describes a process for making the surface of polymeric substrates hydrophilic. The process includes coating the surface with a solution of a "macroinitiator," after which a hydrophilic vinyl monomer solution is then applied and the system activated in order to provide the free radical polymerization of the monomers to the surface.

On a separate subject, a variety of approaches have been described for use in providing coatings upon porous substrates. For instance, Applicant's U.S. Pat. No. 5,744,515 describes the manner in which porous materials such as vascular grafts can be coated with adhesion molecules in order to promote capillary endothelialization once positioned in vivo. In one embodiment, the adhesion molecules themselves bear photoreactive groups, in order to permit the molecules to be contacted with the surface and immobilized upon activation of the photoreactive groups.

A relatively new type of medical device is referred to as a "distal protection device," for use in filtering blood in situ, downstream from the site at which an interventional procedure is being performed. Examples of such devices are described, for instance, in U.S. Pat. No. 6,245,089. However, no teachings appear to exist in the art regarding either the ability or desirability of providing polymeric coatings on such devices, particularly in a manner that does not substantially alter their desired performance characteristics.

Indeed, Applicant has found that the above-described approaches and reagents, whether for attaching derivatized polymers, or for grafting polymers onto surfaces, tend to be of considerably less utility for surfaces having particularly small pores, interstitial spaces or apertures that are intended to remain open and unclogged in the course of their intended use. Such pores and the like can tend to be clogged, particularly by the use of relatively hydrophilic coating agents, which tend to "web" over the apertures, thereby jeopardizing the uniformity and/or utility of the thus-coated article.

To the best of Applicant's knowledge, the art does not teach, nor are there commercial products that involve, the preparation or use of nonpolymeric coating agents that are themselves attached to the porous surface of an article in order to initiate photopolymerization from the surface. Moreover, there remains a need for coating agents that can be used to coat relatively hydrophobic surfaces, and particularly for those surfaces that provide relatively small pores, interstitial spaces, or apertures.

SUMMARY OF INVENTION

The present invention provides a grafting reagent and related method of using the reagent to form a polymeric coating on a support surface, and preferably a porous support surface, in a manner that substantially preserves and/or provides desired properties to the surface, e.g., preserves the desired porosity of the surface. In another aspect, the invention provides a method of priming a support surface with the grafting reagent itself, in a manner adapted to permit the formation of a polymer coating by grafting. The invention also provides a porous surface provided with a grafted polymer coating formed by such a method. Further, the invention provides a grafting system that includes a grafting reagent and polymerizable compounds as described herein.

The reagent and method are particularly useful for forming a thin, conformable, uniform, uncrosslinked coating having desired properties (e.g., a desired combination of such properties as lubricity, hemocompatability, thickness, and wettability) onto the surface of a preformed, and particularly a porous, polymeric substrate. The word "porous," when used in this regard, will be used to generally refer to pores, interstitial spaces, or other apertures or voids of a size and/or configuration that would be substantially occluded (e.g., by webbing) when coated with preformed polymers of a type formed in situ by the grafting method described herein. By "substantially occluded," in this regard, it is meant that the pores would be affected (e.g., filled or constricted) to an extent that would render the surface no longer suitable for its intended use.

In one aspect, the present invention provides a method of forming a polymeric coating on a support surface, the method comprising:

a) providing a support surface, preferably a porous support surface;

b) providing a nonpolymeric grafting reagent comprising at least one photoinitator group, and preferably further comprising one or more latent reactive (e.g., photoreactive) groups adapted to be activated in order covalently attach the grafting reagent to the surface itself, c) providing at least one polymerizable monomer solution adapted to be contacted with the surface, in the presence of the grafting reagent, and to be polymerized upon activation of the photoinitiator; and d) applying the grafting reagent and monomer solution to the surface in a manner, and under conditions, suitable to coat the surface with the grafting reagent and to cause the polymerization of monomers to the surface upon activation of the grafting reagent, and optionally, to attach the grafting reagent to the surface upon activation of the latent reactive (e.g., photoreactive) group(s).

The moieties used to provide the photoinitiator and latent reactive (e.g., photoreactive) groups can be the same or different. For instance, in a preferred embodiment, the reagent includes a plurality of aryl ketone groups, each of which are adapted to serve either function. In such an embodiment, the actual use of any particular group (i.e., whether it will serve as a photoinitiator or photoreactive group) is determined at the time and under the conditions of use. In alternative embodiments, groups such as carbenes and nitrenes can serve as the photoreactive group of a reagent, but are not adapted to photoinitiate monomers of the type described herein. In such an alternative embodiment, at least one photoinitiator group is therefore included as well.

The method according to the present invention provides improved control of the coating process (e.g., as compared to coating preformed polymers) and reduces or avoids many of the deficiencies of previous methods, particularly for use with surfaces providing small pore sizes (e.g., "microporous" surfaces). The present invention provides for the concentration of latent reactive (e.g., photoreactive) and photoinitiating groups directly on the surface of a device thus maximizing the efficiency of these groups and promoting the formation of linear polymer chains (e.g. as compared to a crosslinked matrix which results from the use of preformed latent reactive (e.g., photoreactive) polymers).

The resultant polymeric coating can be selected and adapted so as to provide the surface with desirable features in the course of its manufacture or use, or once positioned in vivo and/or used ex vivo, including permeability, anti-thrombogenicity, lubricity, hemocompatibility, wettability/hydrophilicity, durability of attachment to the surface, biocompatibility, and reduced bacterial adhesion.

In a particularly preferred embodiment, the method and composition are used to coat the surfaces of devices such as emboli catching (also known as "distal protection") devices, of the type described in U.S. Pat. No. 6,245,089, the disclosure of which is incorporated herein by reference. The composition provides particular advantages by being able to suitably coat the surfaces of the porous materials, and thereby alter their physico-chemical features in a desired, controllable fashion, while not unduly clogging the pores in a manner that would render them unsuitable for their intended purpose.

Various steps of the present method can be performed in any suitable manner and order, preferably sequentially. These include the illumination step to attach the grafting reagent to the surface, as well as the step of providing the polymerizable monomers, and the step of illuminating the grafting reagent to initiate polymerization.

DETAILED DESCRIPTION

Support surfaces useful in the method of this invention provide an optimal combination of such physical and mechanical properties as porosity, hydrophobicity/hydrophilicity, strength, flexibility, permeability, elongation, abrasion resistance, and tear resistance.

Examples of materials used to provide suitable support surfaces include polyolefins, polystyrenes, poly(alkyl)methacrylates and poly(alkyl) acrylates, polyacrylonitriles, poly(vinylacetates), poly(vinyl alcohols), chlorine-containing polymers such as poly(vinyl) chloride, polyoxymethylenes, polycarbonates, polyamides, polyimides, polyurethanes, polyvinylidene difluoride (PVDF), phenolics, amino-epoxy resins, polyesters, silicones, polyethylene terephthalates (PET), polyglycolic acids (PGA), poly-(p-phenyleneterephthalamides), polyphosphazenes, polypropylenes, parylenes, silanes, and silicone elastomers, as well as copolymers and combinations thereof, as well as cellulose-based plastics, and rubber-like plastics. See generally, "Plastics," pp. 462-464, in *Concise Encyclopedia of Polymer Science and Engineering*, Kroschwitz, ed., John Wiley and Sons, 1990, the disclosure of which is incorporated herein by reference. Parylene is the generic name for members of a unique polymer (poly-p-xylylene) series, several of which are available commercially (e.g., in the form of "Parylene C", "Parylene D" and Parylene N", from Union Carbide). For example, "Parylene C", is a poly-para-xylylene containing a substituted chlorine atom, and can be used to create a moisture barrier on the surface of a medical device. Parylene C can be coated by delivering it in a vacuum environment at low pressure as a gaseous polymerizable monomer. The monomer condenses and polymerizes on substrates at room temperature, forming a matrix on the surface of the medical device. The coating thickness is controlled by pressure, temperature, and the amount of monomer used, in order to provide an inert, non-reactive barrier. In addition, supports such as those formed of pyrolytic carbon and silylated surfaces of glass, ceramic, or metal are suitable for surface modification.

Such materials can be used to fabricate a number of devices capable of being provided, either before, during and/or after their fabrication, with a polymeric coating according to the present invention. Such devices are typically adapted to be used on either a permanent or transitory basis, and either within or upon the body. Such devices can be entirely coated with the present reagent, or have particular portions or components thus coated.

Medical devices, including those adapted for use within or upon the body, include either those permanently implanted in the body for long-term use or used temporarily in the body are one general class of suitable devices, and include but are not limited to the following.

Long-term devices including grafts, stents, stent/graft combinations, valves, heart assist devices, shunts, and anastomoses devices; catheters such as central venous access catheters; orthopedic devices such as joint implants, fracture repair devices, and artificial tendons, dental implants and dental fracture repair devices; intraocular lenses; surgical devices such as sutures and patches; synthetic prosthesis; and artificial organs such as artificial lung, kidney, and heart devices.

Short-term devices including vascular devices such as distal protection devices; catheters such as acute and chronic hemodialysis catheters, cooling/heating catheters, and percutaneous transluminal coronary angioplasty (PTCA) catheters; ophthalmic devices such as contact lenses and glaucoma drain shunts.

Similarly, non-implanted biomedical devices can be coated, in whole or in part, using a reagent of the present invention, including but not limited to the following. Diagnostic slides such as gene chips, DNA chip arrays, microarrays, protein chips, and fluorescence in situ hybridization (FISH) slides; arrays, including cDNA arrays and oligonucleotide arrays; blood sampling and testing components; functionalized microspheres; tubing and membranes, e.g., for use in dialysis or blood oxygenator equipment; and blood bags, membranes, cell culture devices, chromatographic support materials, biosensors, and the like.

The method and reagent of this invention are particularly well suited for coating devices such as distal protection devices (also known as emboli catching devices), e.g., of the type described in U.S. Pat. No. 6,245,089, the disclosure of which is incorporated herein by reference The present invention provides improved control over the in situ polymerization process, by the use of latent reactive (e.g., photoreactive) species that are capable of serving as both latent reactive (e.g., photoreactive) groups (sufficient to covalently attach the reagent to a surface) and as photoinitiators (e.g., photoinitiating groups to initiate polymerization). As described herein, photoinitiating groups can be provided by the grafting reagent itself, instead of (or optionally, in addition to) being separately provided in solution or by a preformed polymer to be attached to the support surface. The photoinitiating groups of the present invention are adapted to regeneratively participate in the polymerization process.

In a particularly preferred embodiment, the latent reactive (e.g., photoreactive) species are adapted to undergo reversible photolytic activation, thereby permitting latent reactive (e.g., photoreactive) species that are not consumed in attachment to the support surface to revert to an inactive, or "latent" state. These latent reactive (e.g., photoreactive) species can be subsequently activated, in order to serve as photoinitiator groups for initiating free radical polymerization. Thus, excitation of the photoinitiator is reversible and the group can return to a ground state energy level upon removal of the energy source. Particularly preferred photoinitiators are those groups that are subject to multiple activation in suitable (typically aqueous) systems and hence provide increased coating efficiency.

In another preferred embodiment, the photoinitiating species are adapted to undergo a homolytic alpha cleavage reaction between a carbonyl group and an adjacent carbon atom. This type of reaction is generally referred to as a Norrish type I reaction.

In another embodiment, the photoinitiating species is a photosensitizer. Photosensitizers are generally photoreducible or photo-oxidizable dyes. In most instances, photoreducible dyes are used in conjunction with a reductant, typically a tertiary amine. The reductant intercepts the induced triplet, producing the radical anion of the dye and the radical cation of the reductant.

A typical free radical polymerization comprises four steps: initiation, propagation, termination, and chain transfer. In initiation, a free radical derived from an initiator adds to a monomer molecule to form an active center. Other initiating reactions include addition to the head of the molecule or hydrogen abstraction, and the reaction mechanism depends upon the structures of the radical and monomer. The propagation or growth reaction consists of the rapid addition of monomer molecules to the radical species. The most common mechanism of propagation occurs in head-to-tail fashion. However, propagation may also occur in head-to-head, tail-to-head, and tail-to-tail modes. In termination, the polymer chain stops growing by the destruction of propagating radicals. Normally, in the absence of species that destroy radicals, chain termination occurs by bimolecular interaction of radicals (e.g., radical combinations or disproportionation).

In a preferred embodiment, the grafting reagent comprises a restrained, multifunctional grafting reagent, the preparation of which is described in Applicant's U.S. Pat. No. 5,414,075, the entire disclosure of which is incorporated herein by reference. Such a reagent can be used to initially derivatize the support surface, prior to contacting the surface with polymerizable monomer.

A grafting reagent of this preferred type comprises a chemical nonpolymeric core molecule having attached to it one or more first latent reactive groups and one or more second latent reactive groups, each of the first and second latent reactive groups being attached to the backbone in such a manner that, upon activation of the latent reactive groups in the presence of a support surface, a) the first latent reactive groups are capable of covalently bonding to the support surface, and b) upon bonding of the first latent reactive groups to the surface, the second latent reactive groups are;

i) restricted from reacting with either a spacer or the support surface, ii) capable of reverting to their inactive state, and iii) upon reverting to their inactive state, are thereafter capable of being reactivated in order to later initiate polymerization of monomers, thereby forming a polymer on the surface.

The first and second latent reactive groups can be of the same or different types, and as previously, the distinction between the two can be determined under the conditions, and at the time of use. Generally, the first latent reactive groups are defined (from amongst those originally present) as those that become attached to the surface itself, which in turn, serves to define the second latent reactive groups as those that remain unattached, and hence revert to activatable form. In the present invention, Applicants have found that those second latent reactive groups are particularly well suited to serve as photoinitiators for a polymerization reaction. Without intending to be bound by theory, it appears that the utility of such reagents for use in grafting is improved also by the reagent's lack of solubility in polar solvent. In a particularly preferred embodiment, the grafting reagent of the invention is selected from the group consisting of tetrakis (4-benzoylbenzyl ether), the tetrakis (4-benzoylbenzoate ester) of pentaerythritol, and an acylated derivative of tetraphenylmethane.

In an alternative embodiment, the present invention provides a coating agent comprising a nonpolymeric core molecule having attached thereto, either directly or indirectly, one or more substituents comprising negatively charged groups, and two or more latent reactive species, wherein the latent reactive species are provided as discrete latent reactive groups. In such an embodiment, the latent reactive species comprise one or more first latent reactive species adapted to attach the coating agent to a surface, and one or more second latent reactive (e.g., photoreactive) species adapted to initiate photopolymerization. Suitable reagents of this type are described, for instance, in Applicant's International Patent Application No. US 99/21247, the disclosure of which is incorporated herein by reference.

In one such embodiment, the coating agent comprises a conjugated cyclic diketone having attached thereto, either directly or indirectly, one or more substituents comprising negatively charged groups, and wherein each ketone group of the diketone is adapted to serve as a photoreactive moiety capable of being activated in order to provide a free radical. Preferably, the conjugated cyclic diketone is a quinone selected from substituted and unsubstituted benzoquinone, camphorquinone, naphthoquinone, and anthraquinone.

Such reagents typically comprise a nonpolymeric core molecule having attached thereto, either directly or indirectly, one or more substituents comprising negatively charged groups, and two or more latent reactive species, wherein the latent reactive species are provided as discrete photoreactive groups. In a preferred embodiment, such coating agents are selected from the group 4,5-bis(4-benzoylphenylmethyleneoxy) benzene-1,3-disulfonic acid dipotassium salt (DBDS), 2,5-bis(4-benzoylphenylmethyleneoxy) benzene-1,4-disulfonic acid dipotassium salt (DBHQ), a hydroquinone monosulfonic acid derivative, an anthraquinone sulfonic acid salt, and a camphorquinone derivative. Optimally, the coating agent is selected from DBDS, DBHQ, and 2,5-bis(4-benzoylphenylmethyleneoxy) benzene-1-sulfonic acid mono (or di-) sodium salt.

Particularly preferred grafting reagents of this type are selected from the group 4,5-bis(4-benzoylphenylmethyleneoxy) benzene-1,3-disulfonic acid dipotassium salt (DBDS), and 2,5-bis(4-benzoylphenylmethyleneoxy) benzene-1,4-disulfonic acid dipotassium salt (DBHQ).

In another alternative embodiment, a grafting reagent of the present invention can be provided in the form of a reagent of the general formula:

X—Y—X wherein each X is independently a radical containing a latent reactive (e.g., photoreactive) group and Y is a radical containing one or more charged groups. Such reagents are described, for instance, in Applicant's U.S. Pat. No. 5,714,360, the disclosure of which is incorporated herein by reference.

A reagent of this type includes one or more charged groups, and optionally one or more additional latent reactive (e.g., photoreactive) groups, included in the radical identified in the empirical formula as "Y." A "charged" group, when used in this sense, refers to groups that are present in ionic form, i.e., carry an electrical charge under the conditions (e.g., pH) of use. The charged groups are present, in part, to provide the compound with the desired water solubility.

Preferred Y groups are nonpolymeric, that is, they are not formed by polymerization of any combination of monomers. Nonpolymeric agents are preferred since they will tend to have lower molecular mass, which in turn means that they can generally be prepared to have a higher concentration of latent reactive groups per unit mass. In turn, they can generally provide a higher coating density of latent reactive groups than comparable latent reactive polymeric agents.

The type and number of charged groups in a preferred agent are sufficient to provide the agent with a water solubility (at room temperature and optimal pH) of at least about 0.1 mg/ml, and preferably at least about 0.5 mg/ml, and more preferably at least about 1 mg/ml. Given the nature of the surface coating process, linking agent solubility levels of at least about 0.1 mg/ml are generally adequate for providing useful coatings of target molecules on surfaces.

Examples of suitable charged groups include, but are not limited to, salts of organic acids (such as sulfonate, phosphonate, and carboxylate groups), onium compounds (such as quaternary ammonium, sulfonium, and phosphonium groups), and protonated amines, as well as combinations thereof. An example of an agent employing charged groups other than quaternary ammonium compounds is provided in Formula X of Table I in the '360 patent, the disclosure of which is incorporated herein by reference. By reference to the empirical formula provided above, it can be seen that $R^3$ in Formula X would be a lone pair of electrons, in order to provide a tertiary amine group, and $R^2$ would contain a charged sulfonate group in a radical of the formula —$CH_2$—$CH_2$—$SO_3Na$. Sufficient overall charge to render the compound water soluble is provided by the negative charge of the remote sulfonate group.

A preferred charged group for use in preparing compounds of the present invention is a quaternary ammonium group. The term "quaternary ammonium," as used herein, refers to organic derivatives of $NH_4^+$ in which the hydrogen atoms are each replaced by radicals, thereby imparting a net positive charge on the radical. The remaining counter-ion can be provided by any suitable anionic species, such as a chloride, bromide, iodide, or sulfate ion.

In a preferred embodiment two or more photoreactive groups are provided by the X groups attached to the central Y radical. Upon exposure to a suitable light source, each of the photoreactive groups are subject to activation. The term "photoreactive group," as used herein, refers to a chemical group that responds to an applied external ultraviolet or visible light source in order to undergo active specie generation, resulting in covalent bonding to an adjacent chemical structure (via an abstractable hydrogen).

Preferred reagents of this type are selected from the group ethylenebis(4-benzoylbenzyldimethylammonium) dibromide (Diphoto-Diquat); hexamethylenebis(4-benzoylbenzyldimethylammonium) dibromide (Diphoto-Diquat); 1,4-bis(4-benzoylbenzyl)-1,4-dimethylpiperazinediium dibromide (Diphoto-Diquat); bis(4-benzoylbenzyl)hexamethylenetetraminediium dibromide (Diphoto-Diquat); bis[2-(4-benzoylbenzyldimethylammonio)ethyl]-4-benzoylbenzylmethylammonium tribromide (Triphoto-Triquat); 4,4-bis(4-benzoylbenzyl)morpholinium bromide (Diphoto-Monoquat); ethylenebis[(2-(4-benzoylbenzyldimethylammonio)ethyl)-4-benzoylbenzylmethylammonium]tetrabromide (Tetraphoto-Tetraquat); 1,1,4,4-tetrakis(4-benzoylbenzyl)piperazinediium Dibromide (Tetraphoto-Diquat); and N,N-bis[2-(4-benzoylbenzyloxy)ethyl]-2-aminoethanesulfonic acid, sodium salt (Diphoto-Monosulfonate), and analogues (including those having alternative counter ions) thereof, corresponding to Compounds II through X, respectively, of the above-captioned '360 patent. Terms such as "Diphoto-Diquat" are used herein to summarize the number of respective groups (e.g., photo groups, quaternary ammonium groups, etc.) per reagent molecule.

A "latent reactive group," as used herein, refers to a chemical group that responds to an applied external energy source in order to undergo active specie generation, resulting in covalent bonding to an adjacent chemical structure (via an abstractable hydrogen). Preferred groups are sufficiently stable to be stored under conditions in which they retain such properties. See, e.g., U.S. Pat. No. 5,002,582, the disclosure of which is incorporated herein by reference. Latent reactive groups can be chosen that are responsive to various portions of the electromagnetic spectrum, with those responsive to ultraviolet and visible portions of the spectrum (referred to herein as "photoreactive") being particularly preferred.

Photoreactive species respond to a specific applied external ultraviolet or visible light source to undergo active specie generation with resultant covalent bonding to an adjacent chemical structure, e.g., as provided by the same or a different molecule. Photoreactive species are those groups of atoms in a molecule that retain their covalent bonds unchanged under conditions of storage but that, upon activation by a specific applied external ultraviolet or visible light source, form covalent bonds with other molecules.

Latent reactive (e.g., photoreactive) species generate active species such as free radicals and particularly nitrenes, carbenes, and excited states of ketones upon absorption of electromagnetic energy. Latent reactive (e.g., photoreactive) species can be chosen to be responsive to various portions of the electromagnetic spectrum, and photoreactive species that are responsive to the ultraviolet and visible portions of the spectrum are preferred and can be referred to herein occasionally as "photochemical group" or "photogroup."

The latent reactive (e.g., photoreactive) species in latent reactive (e.g., photoreactive) aryl ketones are preferred, such as acetophenone, benzophenone, anthraquinone, anthrone, and anthrone-like heterocycles (i.e., heterocyclic analogs of anthrone such as those having N, O, or S in the 10-position), or their substituted (e.g., ring substituted) derivatives. Examples of preferred aryl ketones include heterocyclic derivatives of anthrone, including acridone, xanthone, and thioxanthone, and their ring substituted derivatives. Particularly preferred are thioxanthone, and its derivatives, having excitation energies greater than about 360 nm.

The functional groups of such ketones are preferred since they are readily capable of undergoing the activation/inactivation/reactivation cycle described herein. Benzophenone is a particularly preferred latent reactive (e.g., photoreactive) moiety, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source. Photoactivatible aryl ketones such as benzophenone and acetophenone are of particular importance inasmuch as these groups are subject to multiple reactivation in water and hence provide increased coating efficiency.

The method of the present invention involves the attachment of a polymerizable compound to a support surface by use of the above-described grafting reagent. As will be discussed more fully below, the grafting reagent can be used in a number of different ways to achieve the desired result.

In one embodiment, the present invention provides a system comprising a grafting reagent as described herein, and a plurality of molecules, each bearing one or more polymerizable groups. In accordance with this embodiment, the photoinitiator group serves to initiate polymerization of the polymerizable groups, thereby forming a polymeric coating, e.g., in the form of a layer covalently bound to the support surface of a desired article via the grafting reagent. As used herein, "polymerizable group" shall generally refer to a group that is adapted to be polymerized by initiation via free radical generation, and more preferably by photoinitiators activated by visible or long wavelength ultraviolet radiation.

Suitable polymerizable compounds can be used to provide polymerization products (e.g., a polymeric coating resulting from free radical polymerization) that are either inherently hydrophilic or are capable of being readily modified to provide hydrophilic characteristics at appropriate reaction conditions (e.g., pH). Moreover, the polymerizable groups of such compounds can include those adapted to participate in free-radical polymerization. Preferred compounds include at least one free-radical polymerizable component (e.g., a vinyl group), and at least one functional group with a high affinity for water. As contemplated by the present invention, such functional groups with a high affinity for water can be negatively charged, positively charged, or electrically neutral.

Suitable polymerizable compounds are selected from monomeric polymerizable molecules (e.g., organic monomers), and macromeric polymerizable molecules (e.g., organic macromers). As used herein, "macromer" shall refer to a macromolecular monomer having a molecular weight of about 250 to about 25,000, and preferably from about 1,000 to about 5,000. For purposes of the present invention, and unless specified otherwise, the term "monomer" when used in this respect shall generally refer to monomeric and/or macromolecular polymerizable molecules.

Suitable polymerizable compounds can contain neutral hydrophilic functional units, for example, acrylamide and methacrylamide derivatives. Examples of suitable monomers containing electrically neutral hydrophilic structural units include acrylamide, methacrylamide, N-alkylacrylamides (e.g., N,N-dimethylacrylamide or methacrylamide), N-vinylpyrrolidinone, N-vinylacetamide, N-vinyl formamide, hydroxyethylacrylate, hydroxyethylmethacrylate, hydroxypropyl acrylate or methacrylate, glycerolmonomethacrylate, and glycerolmonoacrylate.

Alternatively, suitable polymerizable compounds containing electrically charged hydrophilic functional units include molecules whose polymers, once formed, can be readily modified (e.g., by hydrolysis) to provide products with enhanced affinity for water. Examples of suitable monomers of this type include glycidyl acrylate or methacrylate, whose polymers bear epoxy groups that can be readily hydrolyzed to provide glycol structures having a high affinity for water. Examples of suitable monomeric polymerizable molecules that are negatively charged at appropriate pH levels include acrylic acid, methacrylic acid, maleic acid, fumaric acid, itaconic acid, AMPS (acrylamidomethylpropane sulfonic acid), vinyl phosphoric acid, vinylbenzoic acid, and the like.

Alternatively, suitable monomeric polymerizable molecules that are positively charged at appropriate pH levels include molecules whose polymers, once formed, can be readily modified to provide products with enhanced affinity for water. Examples of suitable monomeric molecules that are positively charged at appropriate pH levels include 3-aminopropylmethacrylamide (APMA), methacrylamidopropyltrimethylammonium chloride (MAPTAC), N,N-dimethylaminoethylmethacrylate, N,N-diethylaminoethylacrylate, and the like.

Alternatively, suitable positively charged monomeric polymerizable molecules include those molecules that can be readily modified to provide products with enhanced affinity for water as well as a positive charge, e.g., glycidyl methacrylate whose polymeric products can be reacted with amines (e.g., ethylamine), to provide hydroxyamino compounds. In some cases, these materials will contain a structural unit with an inherent positive charge, as for example with fully quaternized ammonium structures. In other cases, the positively charged structural unit will exist at certain pH values, particularly at acidic pH values.

In yet another embodiment, the polymerizable monomer compounds of the present invention comprise macromeric polymerizable molecules. Suitable macromers can be synthesized from monomers such as those illustrated above. According to the present invention, polymerizable functional components (e.g., vinyl groups) of the macromer can be located at either terminus of the polymer chain, or at one or more points along the polymer chain, in a random or nonrandom structural manner.

The number of free-radical polymerizable groups per molecule can be varied according to the application. For example, it can be preferable to employ a macromer with just one free-radical polymerizable unit. In other instances, however, it can be preferable to employ a macromer with more than one, e.g., two or more polymerizable units per macromer. Additionally, the macromer of the present invention can contain structural features to provide improved affinity for water in a manner typically unavailable in small molecule structures (e.g., hydrophilic poly(ethylene glycol) materials). Examples of suitable macromeric polymerizable compounds include methacrylate derivatives, monoacrylate derivatives, and acrylamide derivatives. Particularly preferred macromeric polymerizable compounds include poly (ethylene glycol)monomethyacrylate, methoxypoly(ethylene glycol)monomethacrylate, poly(ethylene glycol) monoacrylate, methyacrylamidopoly(acrylamide), poly (acrylamide-co-3-methacrylamidopropylacrylamide), poly (vinylalcohol)methacrylate, poly(vinylalcohol)acrylate, poly(vinylalcohol)dimethacrylate, and the like.

Such macromers can be prepared, for instance, by first synthesizing a hydrophilic polymer of the desired molecular weight, followed by a polymer modification step to introduce the desired level of polymerizable (e.g., vinyl) functional units. For example, acrylamide can be copolymerized with specific amounts of 3-aminopropylmethacrylamide comonomer, and the resulting copolymer can then be modified by reaction with methacrylic anhydride to introduce the methacrylamide functional units, thereby producing a useful macromer for purposes of this invention.

Poly(ethylene glycol) of a desired molecular weight can be synthesized or purchased from a commercial source, and modified (e.g., by reaction with methacrylyl chloride or methacrylic anhydride) to introduce the terminal methacrylate ester units to produce a macromer useful in the process of this invention. Some applications can benefit by use of macromers with the polymerizable units located at or near the terminus of the polymer chains, whereas other uses can benefit by having the polymerizable unit(s) located along the hydrophilic polymer chain backbone.

Such monomeric and macromeric polymerizable molecules can be used alone or in combination with each other, including for instance, combinations of macromers with other macromers, monomers with other monomers, or macromers combined with one or more small molecule monomers capable of providing polymeric products with the desired affinity for water. Moreover, the above polymerizable compounds can be provided in the form of amphoteric compounds (e.g., zwitterions), thereby providing both positive and negative charges.

A preferred method of this invention includes the step of applying the grafting reagent and monomer solution to the surface in a manner, and under conditions, suitable to coat the surface, which preferably includes pores. The method also includes the step of contacting the surface with polymerizable monomers, typically in solvent or other solution form, and illuminating the surface in order to cause the polymerization of monomers to the surface upon activation of the grafting reagent.

Grafting reagents of the present invention can be used in any suitable manner, e.g., by simultaneous or sequential attachment of the grafting reagent and polymerizable monomers to a support surface. In a preferred embodiment, the method of this invention involves a two-step process, involving sequential steps in which grafting reagent is first attached to the surface, after which compounds are polymerized thereon using the photoinitiator of the attached agent. One advantage of a sequential approach is that photopolymerization of this sort allows the generation of thin polymeric coatings on the support surface. The resultant polymeric coating is typically highly adherent, uniform in thickness, and is highly durable. Moreover, solutions used to form the polymeric coating can be applied (e.g., via in solution application, dipping, spray coating, knife coating, and roller coating) to any suitable support surface of any surface morphology. The resultant polymeric coating, in turn, can be adapted to cover irregular surfaces as well as smooth, relatively uniform surfaces.

Grafting reagents as described herein can be used to modify any suitable surface. Where the latent reactive group of the agent is a latent reactive (e.g., photoreactive) group of the preferred type, the support surface to be coated preferably provides abstractable hydrogen atoms suitable to enable covalent bonding with the activated group. In another embodiment, the surface can be modified (e.g., by pretreatment with a suitable reagent) to provide abstractable hydrogen atoms on the surface.

The steps of the method can be performed in any suitable order. For example, a multifunctional grafting reagent as described above can physically adhere itself to a suitable support surface by hydrophobic interactions. Upon illumination, the photoreactive groups (e.g., benzophenone groups) undergo covalent bond formation at the support surface by the aforementioned mechanism. With the absence of abstractable hydrogens in proximity to the remaining unbonded photoreactive group(s), and removal of the illumination source, the excited state benzophenone returns to ground state energy. These remaining groups are then capable of being reactivated when the polymerizable compound intended for immobilization is present and when the treated surface is exposed to another round of illumination. This method can be described as a "two-step" approach, where the photoreactive grafting reagent is applied in the first step to create the latent reactive surface, and in the second step, the polymerizable compound is added for attachment to the activated surface.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

Structures

COMPOUND I

Tetrakis (4-benzoylbenzyl ether) of Pentaerythritol

COMPOUND II 4,5-bis(4-benzoyl-phenylmethyleneoxy)benzene-1,3-disulfonic acid dipotassium salt (DBDS)

COMPOUND III

Ethylenebis (4-benzoylbenzyldimethylammonium) Dibromide

EXAMPLE 1

Surface Modification of Polyurethane (PU) by Application of Acrylamide/Acrylamidomethylpropane Sulfonic Acid (AMPS) with Compound I Compound I was prepared according to the method described in Example 1 of U.S. Pat. No. 5,414,075. A coating solution was prepared by dissolving an amount of Compound I at 1 g/l in 100% isopropyl alcohol (IPA). Polyurethane rods (5 cm (2 in.) long, Thermedics) were wiped with an IPA (99% purity) soaked lint-free cloth and allowed to dry. The clean PU rods were then dipped into the Compound I solution, previously prepared as described above, removed from the solution at a steady rate (approximately 2 cm/sec), and allowed to dry for at least 5 minutes.

After applying Compound I to the rods, the rods were placed in a solution containing a mixture of monomers (acrylamide 3% or 7% and AMPS 7% or 3% respectively, weight to volume) in deionized (DI) water. Approximately 8 ml of the monomer mixture was placed in a glass syringe (10 ml, Micro-mate™ interchangeable hypodermic syringe with lever lock, Popper and Sons, Inc.) containing a stopcock in the bottom to prevent the solution from draining out. The PU rods were placed in the syringe containing the monomer solution and nitrogen gas was allowed to bubble up into the solution for at least 10 minutes to remove oxygen in the solution. After deoxygenating, the solution containing the PU rods was exposed to UV light (EFOS light—Ultracure 100 SS Plus systems with light guide, EFOS USA Inc. in the 320-500 nm wavelength range for 150 seconds). The intensity of the light, as measured with a radiometer (International Light, IL1400A with SEL005/NS335/W), was approximately 20 mw/cm$^2$ in the 330-340 nm wavelength measured at a distance of 2.5-3.0 cm from the end of the light source. After exposure to the UV light, the samples were removed from the monomer solution and washed thoroughly to remove any unbound residual monomer.

Lubricity and Durability

Figure 1:
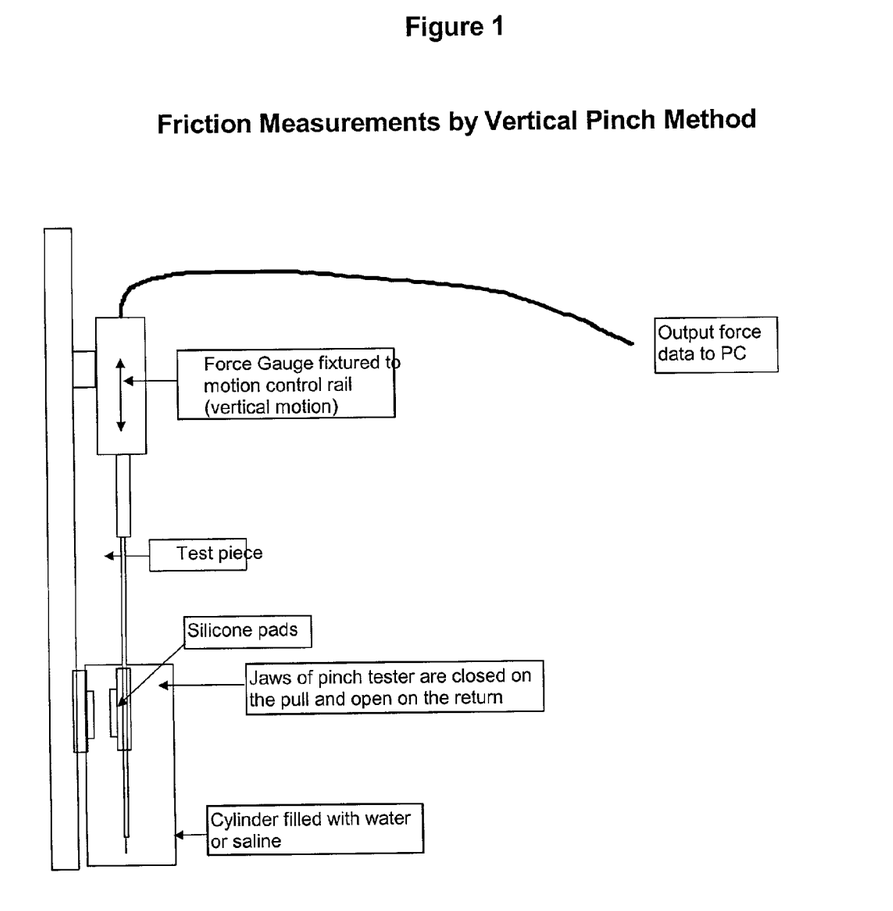
FIG. 1 shows a schematic diagram of a device for performing friction measurements by the vertical pinch method described herein.

After coating, the PU rods were evaluated for lubricity/durability by friction measurements using a Vertical Pinch Method (FIG. 1) described as follows: The coated PU rods were inserted into the end of a rod holder which was placed between the two jaws of a pinch tester which was immersed in a cylinder of water or saline. The jaws of the pinch tester were closed as the sample was pulled in a vertical direction and opened when the coated sample was returned to the original position. A 300 g force (load) was applied as the sample rod was pulled up through the pinched jaws. The average frictional force was determined for 15 cycles while the coated rod traveled 3 cm at a travel rate of 0.5 mm/sec.

The results shown in Table 1 indicate that the applied coating improved the lubricity of the rods as compared to uncoated controls. The results also show that the coating remained lubricious over the 15 cycles indicating that the coating was also durable.

TABLE 1

Lubricity/Durability Testing

| Substrate | Cycle 1 Friction Force (grams) | Cycle 15 Friction Force (grams) | % Increase (Cycle 1 to 15) | Average of 15 Cycles (grams) | % Force Reduction (compared to uncoated) |
|---|---|---|---|---|---|
| Polyurethane-uncoated n = 1 | — | — | — | 190.6 | |
| Polyurethane-graft coating (7% AMPS 3% Acrylamide) n = 3 | 6.7 | 6.5 | -2.7 | 6.5 | 96.6 |
| PEBAX-uncoated n = 2 | — | — | — | 190.3 | |
| PEBAX-graft coating (7% AMPS 3% Acrylamide) n = 3 | 9.1 | 10.2 | 12.2 | 9.5 | 95.0 |
| Silicone-uncoated n = 3 | — | — | — | 157.6 | |
| Silicone-graft coating (3% AMPS 7% Acrylamide) N = 8 | 21.5 | 19.4 | -9.8 | 19.1 | 87.9 |

TABLE 2

Bacterial Adherence Assay

| Substrate | Organism | % Reduction compared to uncoated (n = 6) | P value (one-tailed, alpha = 0.05) |
|---|---|---|---|
| Polyurethane | S. epidermidis | 97.9 | 0.0034 |
| Polyurethane | C. albicans | 99.1 | 0.0392 |
| Polyurethane | P. mirabilis | 99.6 | 0.0063 |
| PEBAX | S. epidermidis | 96.7 | 0.1104 |
| PEBAX | C. albicans | 96.0 | 0.0167 |
| PEBAX | P. mirabilis | 99.6 | 0.1112 |
| Silicone | S. epidermidis | 82.8 | 0.0408 |

Bacterial Adherence Assays

Bacterial adherence assays of the resulting coated PU rods were performed in the following manner. Three strains of bacteria, *Pseudomonas mirabilis* (ATCC 35506), *Staphylococcus epidermidis* (ATCC RP62A), and *Candida albicans* (ATCC 64550) were examined with the coated rods. Samples were individually placed into snap-cap tubes whereupon three milliliters of 1×10$^7$ CFU/ml prepared suspension of each bacteria was added. Tubes were placed in a rack onto an orbital shaker set at 150 rpm for two hours. Samples were then removed from the tubes and placed into 50 ml screw cap centrifuge tubes in like groups with 40 ml of phosphate buffered saline (PBS, pH 6.8) at room temperature. Caps were screwed on and samples were placed on an orbital shaker at 200 rpm for two minutes. The PBS was decontaminated and this step was repeated three more times. After completion of the wash step, the samples were placed on 100% IPA treated Kimwipes® and dried in a laminar flow hood on Kimwipes® before being imbedded into molten (55° C.) Tryptic Soy Agar with 0.001% TTC (2,3,5-triphenyltetrazolium chloride, Difco). The solidified agar plates were placed in a 37° C. incubator overnight and the colonies were counted the following day. Each sample was sectioned into 8 pie pieces by hand, drawing lines on the petri dish directly above the samples. With the use of a stereoscope and a hand tally counter, each section was counted for colony forming units and the percent reduction as compared to uncoated sample was determined. As indicated in Table 2, the coated rods were significantly less adherent to the three organisms tested as compared to uncoated surfaces.

EXAMPLE 2

Surface Modification of Polyether Block Amide (PEBAX) by Application of Acrylamide/AMPS with Compound I A coating solution was prepared by dissolving Compound I as described in Example 1. PEBAX rods (5 cm O.D. 118, Light Blue, 20% Barium Sulfate, Medical Profiles Inc.) were coated as described in Example 1 except the rods were allowed to soak for approximately 30 minutes in Compound I coating solution. The results for lubricity/durability and bacterial adherence are shown on Table 1 and Table 2, respectively. The results shown in Table 1 indicate that the applied coating improved the lubricity of the rods as compared to uncoated controls. The results of Table 2 indicated that the control rods were not adherent to the three organisms tested, as compared to uncoated rods.

EXAMPLE 3

Surface Modification of Silicone Rubber (SR) by Application of Acrylamide/AMPS with Compound I A coating solution containing Compound I was prepared as described in Example 1. SR rods (5 cm, SSF-19ETD-750, Specialty Silicone Fabricators) were coated by the same procedure as in Example 1 with the following exceptions. The SR rods to be coated were sonicated in an IPA solution for at least 10 minutes. After sonication, the rods were allowed to dry for 2 to 3 hours. The rods were also cleaned with an IPA-soaked lint-free cloth prior to coating with Compound I coating solution. The SR rods were allowed to soak for approximately 30 minutes in the Compound I coating solution. The experimental results for both lubricity/durability and bacterial adherence properties are shown in Table 1 and Table 2, respectively. The results shown in Table 1 and Table 2 indicate that the coated rods were more lubricious and significantly less adherent to the three organisms as compared with uncoated controls.

EXAMPLE 4

Surface Modification and Analysis of Low Density Polyethylene (LDPE) by Application of Acrylamide/AMPS with Compound I Low density polyethylene (LDPE) was precoated with a solution containing Compound I. The polyethylene substrate was obtained as flat sheets (0.3/mm thick), and used as ½ inch diameter disks. The coating solution of Compound I was prepared and coated on the LDPE surface as described in Example 1. After precoating, the LDPE disks were coated with acrylamide/AMPS as previously described (Example 1), after which the coated LDPE pieces were stained in 0.1% Toluidine Blue (Sigma, PN:T3260) for approximately 60 seconds. Visual examination revealed that the coated LDPE material was evenly stained blue, indicating an even and uniform coating. The coated samples were then tested for hemocompatibility using the protocols described below.

Platelet Attachment and Activation from Platelet Rich Plasma

Various samples of the surface-modified materials described above were incubated with platelet rich plasma (PRP), observed with fluorescent microscopy, and imaged with a digital camera to determine the influence of surface chemistry on platelet activation and attachment. Blood was collected fresh from human volunteers into tubes (Vacutainer blood collection tubes, Baxter, product #369705) containing 3.8% (v/v) sodium citrate solution using 9:1 ratio of blood to anticoagulant. The blood was centrifuged at 1200 rpm for 15 minutes to separate PRP from blood. The PRP was collected and kept (less than 1 hour) at room temperature until used.

The test samples (1.5 cm×1.5 cm) were placed in a 12-well plate, 1 sample per well. The PRP solution was added to the samples (150 µl) until the entire surface of each sample was covered, and the samples were then incubated one hour at room temperature with no agitation. After incubation, the PRP was removed carefully by aspiration and 3 ml of Tyrode's buffer (138 mM NaCl, 2.9 mM KCl, 12 mM sodium bicarbonate, 1% (w/v) glucose, pH 7.4) was gently added to each well. The plates were agitated slightly on an orbital shaker for 15 minutes; the solution was changed and the wash repeated. The wash solution was aspirated and 2 ml of 3.7% (v/v) formaldehyde in phosphate buffered saline (PBS) (2 mM $KH_2PO_4$, 8 mM $K_2HPO_4$, 150 mM NaCl, pH 7.4) were added to each well. The plates were incubated for 20 minutes with slight agitation on an orbital shaker at room temperature.

The formaldehyde solution was aspirated off and the samples were rinsed once in deionized water. The cell membranes of the platelets were permeabilized by adding 1 ml of a solution of 1% (v/v) Triton-X 100 (t-octylphenoxypolyethoxyethanol, Sigma 9002-93-1) in PBS and incubated for 15 minutes on an orbital shaker at room temperature. The Triton-X 100 solution was aspirated off of the samples and the samples were rinsed three times with 3 ml PBS each. Phalloidin-Texas Red stock (Molecular Probes, T-7471) was diluted 1:80 in PBS and 400 µl was added to each sample. The plate was incubated in the dark for 20 minutes with slight agitation on an orbital shaker at room temperature. Samples were rinsed 3 times with 3 ml PBS each and once with deionized water. Samples were kept in deionized water until they were viewed with a fluorescence microscope. Images were taken of different areas of the sample with a digital camera at a magnification of 500× to give a representative view of each sample. Percent platelet coverage was measured by analyzing images using Image-Pro Plus software (Media Cybernetics). See Table 3.

TABLE 3

Platelet Attachment

| Sample | % Platelet Coverage (n = 3) | Standard Deviation | % Reduction (compared to uncoated) |
|---|---|---|---|
| Uncoated exp 1 | 62.3 | 3.1 | — |
| Compound I, 7/3 Acrylamide/AMPS-exp 1 | 2 | 0 | 97 |
| Uncoated exp 2 | 54 | 10.4 | — |
| Compound I, 7/3 Acrylamide/AMPS-exp 2 | 0.4 | 0.5 | 99 |

Fibrinogen Adsorption Out of Platelet Poor Plasma (PPP)

Fibrinogen adsorption was quantified using an ELISA technique. First, fibrinogen was adsorbed to samples (uncoated and surface-modified) out of human plasma. Second, the adsorbed fibrinogen was then challenged with a polyclonal anti-human-fibrinogen-HRP (horseradish peroxidase) conjugate. The antibody conjugate generated color upon the addition of chromogenic substrate. Absorbances were then measured using a spectrophotometer. The amount of color generation was proportional to the amount of fibrinogen adsorbed.

Samples were placed in 12×75 mm glass test tubes (3 samples/test tube). One milliliter of human platelet poor plasma (George King Bio-Medical, pooled normal plasma) was added to each test tube. Samples were incubated for 2 hours with agitation on an orbital shaker at room temperature. The plasma was aspirated off of the samples and the samples were washed 2 times with TNT wash solution (50 mM Tris, 150 mM NaCl, 0.05% (v/v) Tween 20, pH 7.5). One milliliter of polyclonal anti-human-fibrinogen-HRP (BioDesign, product #K90056P) was added to each test tube at a dilution of 1:10,000 in Tris-saline (TN) buffered solution (50 mM Tris, 150 mM NaCl, 0.05% (v/v)). Samples were incubated for 30 minutes with agitation on an orbital shaker at room temperature. The antibody solution was aspirated off and the samples were washed three times with TNT wash solution.

Samples were then transferred to clean 12×75 mm glass test tubes (1 sample/test tube) and 1 ml of tetramethylbenzidine (TMB) substrate solution and hydrogen peroxide were added to each test tube. The samples were incubated for 15 minutes with agitation on an orbital shaker at room temperature. The supernatant was then transferred to a 96-well microtiter plate and the absorbances at 650 mm were read on a spectrophotometer (Molecular Devices, Thermomax microplate reader) with a negative control solution containing chromogen but no conjugate used as the blank. The absorbances are directly proportional to the surface concentration of HRP and, therefore, also proportional to the surface concentration of fibrinogen bound to the surface of the materials. The results are shown in Table 4.

TABLE 4

Fibrinogen binding

| Sample | Mean ± SD (Absorbance at 650 nm) n = 3 | % Reduction (compared to uncoated) |
|---|---|---|
| Uncoated | 0.294 ± 0.024 | — |
| Compound I, 7/3 Acrylamide/AMPS | 0.113 ± 0.019 | 61 |

Factor XIIa Generation—A Measure of Contact Activation

The uncoated and surface-modified low-density polyethylene (LDPE) samples were assayed for Factor XIIa (activated Factor XII) generation, a measure of contact activation of the intrinsic coagulation cascade. Human plasma was incubated on samples for 1 hour. Samples of the plasma were removed and transferred to a 96-well plate. A chromogenic substrate that is specific for factor XIIa was added to the wells. Absorbances were measured using a spectrophotometer and factor XIIa generation was proportional to the amount of color generated.

Human platelet-poor plasma (George King Bio-Medical Inc., pooled normal plasma) was diluted 4 times in Tris-buffered saline (TBS), 50 mM Tris, 150 mM NaCl, pH 7.5, to obtain 25% plasma. Samples (25 mm diameter uncoated LDPE, surface-modified LDPE, and glass disks) were placed in a 6-well plate (1 disk/well). Glass disks served as a positive control because factor XII is greatly activated by negatively charged surfaces. 500 µl aliquots of 25% plasma were carefully placed on the disks to ensure the plasma only contacted the disks and not the 6-well plate. The samples were incubated for 2 hours at room temperature with no agitation. The incubated plasma was removed and stored at −80° C. until the assay was performed.

The substrate for the assay, Z-Lys-Phe-Arg-pNA.2HCl (Calbiochem, product #03-32-0073) was dissolved in TBS and stored in aliquots of 1 mg/ml at −80° C. The frozen plasma samples were thawed and diluted 5 times with TBS. From the 5 times diluted plasma samples, 50 µl plasma was transferred to a 96-well plate. In the wells containing 50 µl plasma, 50 µl of 800 KIU/ml aprotinin (Calbiochem, product #616398) was added to inhibit substrate cleavage by kallikrein. Thus, all plasma samples were diluted 40 times and had 100 µl volume. The diluted plasma samples were then mixed 1:1 with TBS diluted substrate.

The amount of factor XIIa proteolytic activity generated during incubation at 37° C., inducing release of the yellow-colored pNA, was recorded at 405 nm in 30 second time intervals for 30 minutes (Molecular Devices, Thermomax microplate reader and SoftMax-Pro software). Results were expressed as mO.D./minute. A positive control was obtained by incubation of plasma with kaolin. To 1 ml of diluted (25% v/v) plasma, 10 mg kaolin (Sigma, product #K-7375) was added, thoroughly shaken for 10 seconds, and incubated for 5 minutes with agitation on an orbital shaker at 37° C. After incubation, the plasma was centrifuged for 30 seconds at 3,000 g. The plasma was transferred to a clean microcentrifuge test tube and stored at −80° C. until factor XIIa activity measurements were performed. The results are shown in Table 5.

TABLE 5

Factor XIIa Generation

| Sample | Contact Activation (mOD/min) n = 3 | % Reduction (compared to + control) |
|---|---|---|
| LDPE (negative control) | 0 | 100 |
| Glass (positive control) | 1.73 | — |
| Compound I, 7/3 Acrylamide/AMPS graft | 0.11 | 93.4 |

The results shown in Tables 3-5 indicated that the acrylamide/AMPS coatings on the LDPE disks pretreated with Compound I were hemocompatible using the in vitro evaluations previously described.

EXAMPLE 5

Surface Modification of PU by Application of Acrylamide/AMPS with Compound II A reagent of the structure shown as Compound II above was prepared in the manner described in Example 1 of U.S. Pat. No. 6,278,018.

A coating solution was prepared containing 5 mg/ml of Compound II in DI water. PU rods (5 cm, Pellethane, EG-60D, Thermedics) were cleaned with IPA (>99% purity) using a lint-free cloth and allowed to dry. The clean rods were placed in a clear glass tube containing the Compound II solution. The rods were incubated in the solution at room temperature for approximately five minutes.

Following incubation, the substrate in the Compound II solution was illuminated with a Dymax flood lamp (model no. 2000 EC, Dymax Corporation, Torrington, Conn.) which contained a doped mercury vapor lamp, to activate the photoreactive groups present in Compound II, thereby attaching it to the rod surface as a base coat. The rods were illuminated for three minutes at an intensity of 1-1.5 mW/cm$^2$ in the wavelength range of 330-340 nm at the rod position. After UV curing, the rods were rinsed in DI water for approximately 30 seconds prior to graft polymerization.

Following the coating of the rods with the Compound II base coat, the rods were placed in 8.0 ml of a mixture of acrylamide (0-10%, Aldrich) and AMPS (0-10% AMPS 2405 monomer, salt solution, Lubrizol) contained in a 10 ml glass syringe (Micro-mate interchangeable hypodermic syringe with leur lock, Popper and Sons, Inc.) The monomer mixture and the substrate were then deoxygenated using nitrogen gas bubbling up from the bottom of the syringe for 10 minutes. After 10 minutes of sparging the monomer solution with nitrogen, an EFOS UV light was placed at the top of the syringe.

The solution was illuminated with the EFOS light while nitrogen gas was still bubbling up through the monomer solution. The solution was illuminated for 150 seconds at an intensity of 10 mW/cm$^2$, as measured with a Radiometer (International Light, IL1400A with SEL005/NS335/W), in the 330-340 nm wavelength at a distance of 3.0 cm from the end of the light guide. After exposing to the UV illumination, the rods were removed from the grafting solution and washed in DI water to remove any unbound monomer.

Lubricity and Durability

After coating, the rods were evaluated for lubricity/durability by friction measurements as described in Example 1. The results shown in Table 6 indicated that the coating improved the lubricity of the substrate over uncoated substrate. The results also indicated that the coating remained lubricious over 15 cycles indicating a durable coating.

TABLE 6

Lubricity/Durability Testing

| Substrate | Cycle 1 Friction Force (grams) | Cycle 15 Friction Force (grams) | % Increase (Cycle 1 to 15) | Average of 15 Cycles (grams) | % Force Reduction (compared to uncoated) |
|---|---|---|---|---|---|
| Polyurethane-uncoated n = 1 | — | — | — | 190.6 | |
| Polyurethane Compound II 1 mg/ml 7% Acrylamide 3% AMPS graft n = 3 | 6.7 | 5.9 | −12.2 | 5.9 | 96.9 |
| Polyurethane Compound II 5 mg/ml 7% Acrylamide 3% AMPS graft n = 3 | 3.8 | 3.6 | −5.3 | 3.6 | 98.1 |
| PEBAX-uncoated n = 2 | — | — | — | 190.3 | |
| PEBAX Compound II 1 mg/ml 7% Acrylamide 3% AMPS graft n = 3 | 11.9 | 17.5 | 47.1 | 14.3 | 92.3 |
| PEBAX Compound II 5 mg/ml 7% Acrylamide 3% AMPS graft n = 3 | 7.1 | 8.0 | 12.7 | 7.5 | 96.1 |
| Silicone-uncoated n = 3 | — | — | — | 157.6 | — |
| Silicone Compound II 1 mg/ml 7% Acrylamide 3% AMPS graft n = 3 | 21.2 | 20.1 | −5.2 | 19.8 | 92.1 |

Bacterial Adherence

Bacterial adherence experiments for the monomer grafted PU rods were evaluated as described in Example 1. The bacterial adherence results in Table 7 indicate that the resulting graft coatings were significantly less adherent to the three organisms tested as compared to uncoated surfaces.

TABLE 7

Bacterial Adherence Assay

| Substrate-coating | Organism | % Reduction compared to uncoated (n = 6) |
|---|---|---|
| Polyurethane Compound II 1 mg/ml 7% Acrylamide 3% AMPS graft n = 6 | S. epidermidis | 96.3 |
| Polyurethane Compound II 1 mg/ml 7% Acrylamide 3% AMPS graft n = 6 | C. albicans | 97.3 |
| Polyurethane Compound II 1 mg/ml 7% Acrylamide 3% AMPS graft n = 6 | P. mirabilis | 99.3 |
| PEBAX Compound II 1 mg/ml 10% AMPS n = 6 | S. epidermidis | 97.7 |
| PEBAX Compound II 1 mg/ml 7% Acrylamide 3% AMPS graft n = 6 | C. albicans | 99.0 |
| PEBAX Compound II 1 mg/ml 10% AMPS graft n = 6 | P. mirabilis | 96.0 |

TABLE 7-continued

Bacterial Adherence Assay

| Substrate-coating | Organism | % Reduction compared to uncoated (n = 6) |
|---|---|---|
| Silicone Compound II 1 mg/ml 7% Acrylamide 3% AMPS graft n = 6 | S. epidermidis | 78.3 |

EXAMPLE 6

Surface Modification of PEBAX by Application of Acrylamide/AMPS with Compound II PEBAX rods (Medical Profiles, Inc.) were coated as described in Example 5. The results for lubricity/durability and bacterial adherence are shown in Table 6 and Table 7, respectively. The graft coatings on the PEBAX improved both lubricity/durability and significantly reduced bacterial adherence.

EXAMPLE 7

Surface Modification of Silicone Rubber (SR) by Application of Acrylamide/AMPS with Compound II Silicone rubber (SR) rods were obtained and coated as described in Example 5. The results of studies for lubricity/durability and bacterial adherence are shown in Table 6 and Table 7, respectively. The results of the coatings on SR again indicated improved lubricity and durability over uncoated material and the resulting graft coating was significantly less adherent to the three organisms tested as compared to uncoated surfaces.

EXAMPLE 8

Surface Modification and Hemocompatibility Analysis of LDPE Coated with Acrylamide/AMPS and Compound II Low density polyethylene disks were precoated with Compound II and graft coated with acrylamide/AMPS as described in Example 5. After coating, the disks were evaluated for in vitro hemocompatibility properties including platelet adhesion, fibrinogen binding, and Factor XIIa generation as previously described (Example 4). The results shown in Tables 8-10 indicate that grafting with acrylamide/AMPS on polyethylene pretreated with Compound II was hemocompatible using in vitro evaluations.

TABLE 8

Platelet Adhesion

| Sample | % Platelet Coverage (n = 3) | Standard Deviation | % Reduction (compared to uncoated) |
|---|---|---|---|
| Uncoated exp 1 | 62.3 | 3.1 | — |
| Compound II 1 mg/ml 7/3 Acrylamide/AMPS graft exp 1 | 0.3 | 0.3 | >99 |

TABLE 8-continued

Platelet Adhesion

| Sample | % Platelet Coverage (n = 3) | Standard Deviation | % Reduction (compared to uncoated) |
|---|---|---|---|
| Uncoated exp 2 | 54 | 10.4 | — |
| Compound II 1 mg/ml 7/3 Acrylamide/AMPS graft exp 2 | 0.06 | 0 | >99 |

TABLE 9

Fibrinogen binding

| Sample | Mean ± SD (Absorbance at 650 nm) n = 3 | % Reduction (compared to uncoated) |
|---|---|---|
| Uncoated | 0.294 ± 0.024 | — |
| Compound II 1 mg/ml 7/3 Acrylamide/AMPS graft | 0.095 ± 0.019 | 68 |

TABLE 10

Factor XIIa Generation

| Sample | Contact Activation (mOD/min) n = 3 | % Reduction (compared to + control) |
|---|---|---|
| LDPE (negative control) | 0 | 100 |
| Glass (positive control) | 1.73 | — |
| Compound II 1 mg/ml 7/3 Acrylamide/AMPS graft | 0.38 | 78.0 |

EXAMPLE 9

Surface Modification and Hemocompatibility Analysis of LDPE Coated with Acrylamide/AMPS Pretreated with Compound I or Compound II Low density polyethylene rods were precoated with Compound I or Compound II as previously described in Example 4 and Example 8, respectively. After pretreatment, the rods were graft coated with acrylamide/AMPS as described in Example 5 and evaluated for platelet adhesion and activated coagulation time as described below.

Evaluation of Radiolabeled Platelet Adhesion and Activated Coagulation Time

Fresh bovine blood was obtained from an abattoir and collected into collapsible containers containing heparin. Final concentration of heparin was 1.5 U/ml. For each experiment, 10 L blood was collected and divided into three 3.3 L portions. The test circuit contained ⅜ inch tubing into which test rods were inserted and sealed with epoxy. There were 4 rods per experiment and 8 replicates. Of the 4 rods per experiment, 3 were coated samples and 1 was an uncoated control. The rods were placed in re-circulation conduits and maintained at 37° C. Blood flow in the loop was achieved with the help of a bypass roller pump. The flow rate was 640 ml/min, giving an average flow velocity of 15 cm/s. The three test circuits were run simultaneously under identical test conditions. The blood circulation in the three circuits was maintained for 75 minutes. When the experiment was terminated, the rods were retrieved carefully from the test circuit, examined and photographed with a digital camera. Thrombosis on the rods was evaluated.

To assess thrombosis, the platelets from autologous blood were radiolabeled with $^{111}$Indium before the initiation of the experiment. After adding 45 ml acid citrate dextrose (ACD) to 255 ml blood taken from the 10 L pool, the blood was centrifuged at 350 g for 15 min. This resulted in the sedimentation of the red cells at the bottom of the centrifuge tubes. The supernatant, containing platelet-rich plasma (PRP) was separated from the sediment red cells into other empty centrifuge tubes using a pipette. The separated PRP was then centrifuged at 850 g for 15 min. This sedimented the platelets to the bottom of the tubes to form a pellet. After decanting the supernatant plasma which was free of platelets, the platelets at the bottom of the tubes were suspended by gently swirling the platelet pellets in 2 ml ACD-saline solution (5% ACD (v/v)). Radioactive label—$^{111}$Indium oxine (100 µCi)—was then added to the suspended platelets and incubated at 37° C. for 30 minutes. The radiolabeled platelets were then added back to the blood. Retrieved rods, after being photographed, were cut into small segments (2 to 3 cm each) and placed in counting vials for Gamma counting.

TABLE 11

% CPM (radiolabeled platelet counts per minute) and ACT (activated coagulation time)

| Experiment | Uncoated | Compound II 7/3 graft | Compound I 7/3 graft | ACT |
|---|---|---|---|---|
| 1 | 13.78 | 6.05 | 14.22 | 250 |
| 2 | 96.48 | 0.51 | 1.75 | 251 |
| 3 | 88.16 | 4.40 | 3.10 | 237 |
| 4 | 62.56 | 8.68 | 12.62 | 309 |
| 5 | 52.65 | 11.72 | 11.25 | 296 |
| 6 | 77.93 | 5.45 | 4.32 | 287 |
| 7 | 89.57 | 0.19 | 7.70 | 284 |
| 8 | 98.89 | 0.23 | 0.51 | 306 |
| Average | 72.50 | 4.65 | 6.93 | 278 |
| Std Dev | 28.73 | 4.23 | 5.27 | 28 |
| Excluding Exp. 1 | | | | |
| Average | 80.89 | 4.45 | 5.89 | 281 |
| Std Dev | 17.50 | 4.53 | 4.72 | 27 |

These results indicate that both Compound I and Compound II served as a successful precursor to grafting with a monomer mixture of acrylamide and AMPS. The resulting coating showed a statistical improvement in hemocompatible performance over uncoated PE material.

EXAMPLE 10

Surface Modification of Silicone Rubber (SR) by Application of Acrylamide or Methoxy Polyethyleneglycol (PEG) 1000 Monomethylmethacrylate (MMA) with Compound III A reagent according to the structure of Compound III was prepared in the manner described in Example 2 of U.S. Pat. No. 5,714,360.

A coating solution was prepared by dissolving Compound III at 0.5 mg/ml in DI water. A silicone contact lens was placed in a vial containing an aluminum cap containing 2 ml of the Compound III coating solution. The lens was incubated in the Compound III coating solution for approximately 5 minutes. Following incubation, the silicone in the Compound III solution was placed under a Dymax® flood lamp with UV output of 1-1.5 mW/cm$^2$ (330-340 nm wavelength) at the lens position. The silicone remained under UV light for 1 minute. The silicone was then removed from the UV light, flipped, and placed back under UV light for an additional minute. The lens was rinsed and placed in DI water before grafting with acrylamide or PEG 1000.

Following the Compound III base coat, the silicone was placed in 8 ml of 12% methoxy PEG 1000 MMA solution (in DI water) or a 10% acrylamide solution (in DI water) contained in a 20 ml Fortuna brand syringe. The silicone device in the graft solution was deoxygenated using nitrogen gas bubbling up from the bottom of the syringe for 10 minutes. After 10 minutes of sparging with nitrogen, an EFOS UV light was placed at the top of the syringe. While nitrogen gas was still bubbling up through the solution, the EFOS light was turned on for 1-10 minutes. The UV intensity of the EFOS light, with a 320-390 nm filter, at the level of the solution was 4-6 mW/cm$^2$.

Extensive washing of the lenses under a flow of deionized (DI) water and rubbing the surface between the thumb and forefinger (approx. 30 seconds) indicated a strongly adherent and lubricious layer for both the PEG and acrylamide grafted lenses. (See Table 12)

TABLE 12

Polyethyleneglycol and Acrylamide Grafted Contact Lenses

| Coating | Observation-finger rubbing |
|---|---|
| Compound III 0.5 mg/ml 12% Methoxy PEG 1000 MMA graft | Very slippery and durable, little to no swelling of the silicone |
| Compound III 0.5 mg/ml 10% Acrylamide graft | Very slippery and durable, silicone material swelled. |

EXAMPLE 11

Comparison of Coating Thickness Variance of PEBAX Rods Graft Coated with Compound II/Acrylamide—AMPS and Photocrosslinkable Photopolymers PEBAX rods (Medical Profiles, Inc.) were graft-coated with Compound II and acrylamide/AMPS as described in Example 6 or coated with a "PhotoLink" cocktail consisting of photopolyvinylpyrrolidone (SurModics Product PV05), polyvinylpyrrolidone (Kollidon 90F, BASF), photopolyacrylamide (SurModics Product PA05), and ethylenebis (4-benzoylbenzyldimethylammonium) dibromide (SurModics Product PR03). The coated samples, along with a sample of uncoated substrate, were examined by scanning electron microscopy (SEM) and atomic force microscopy (AFM).

SEM analysis was conducted using a Hitachi S-800 instrument with a field emission electron gun. The coated rods of PEBAX were first sliced with a razor blade at a 45 degree angle to produce a sharp tip on the end of the rod. The tip area was then sliced at 90 degrees with Leica Ultramicrotome fitted with a diamond knife. This process reduced the shear stresses in the slicing process, and produced a flat area on the tip that contained both the coating and the substrate. After the samples were sputter coated with 5 nm of platinum, the microtomed area was imaged in the SEM.

Using this process, the PhotoLink coating was readily visible, with a coating thickness of about 500 nm (0.5 µm). The result agrees with other PhotoLink coatings, which range in thickness from 0.2 to 1 µm. However, the graft coating was not visible using this process. It was concluded that the coating thickness of the graft coatings must fall below the resolution of the specific method described here (Hitachi S-800 electron microscope and ultramicrotome process). From experience, this method can image coatings thicker than 50 to 100 nm, but cannot image coatings thinner than 50-100 nm. Thus, a conservative estimate is that the graft coatings were thinner than about 100 nm.

Atomic force microscopy (AFM) results corroborate the SEM results. AFM analysis of surface roughness was conducted on uncoated, graft coated, and PhotoLink coated samples using a Digital Instruments 3100 AFM. The PEBAX rods were mounted in the AFM, and a 25 $\mu m^2$ area on each sample was examined using the "tapping mode" to avoid damaging the coatings during analysis.

The uncoated PEBAX rods are rough, with about a 200 nm difference between the highest peaks and lowest valleys. Upon coating with the graft coating, the small-scale roughness disappears, leaving only a smoothed version of the large-scale roughness. In other words, upon coating with the graft coating, the surface texture becomes smoother and appears as a "sand dune" type of texture. The results suggest the coating thickness is greater than 10 nm but noticeably less than the peak to valley measurement of 200 nm. Thus, the AFM results corroborate the electron microscope result (coating thickness less than 100 nm). Upon coating with the PhotoLink coating, all of the roughness exhibited by the PEBAX substrate disappeared, since the PhotoLink coatings are thicker than the roughest features of the substrate (200 nm) and thus cover up the roughness of the PEBAX surface.

Since the graft coated surfaces exhibit both lubricity and hemocompatibility, it can be assumed that the coatings are very thin, exhibiting thickness of 100 nm or less.

What is claimed is:

1. A porous support surface bearing a polymeric coating prepared according to a method comprising the steps of:
    a) providing a porous support surface;
    b) providing a nonpolymeric grafting reagent comprising at least two photoinitiator groups, the grafting reagent having one or more substituents comprising positively charged groups;
    c) providing at least one polymerizable monomer solution to be contacted with the surface, in the presence of the grafting reagent, and to be polymerized upon activation of the photoinitiator; and
    d) applying the grafting reagent and monomer solution to the surface to coat the surface with the grafting reagent and to cause the polymerization of monomers to the surface upon activation of the grafting reagent,
wherein the polymeric coating is covalently attached to the surface by the residues of one or more photoinitiator groups provided by the grafting reagent and the polymeric coating is less than about 100 nanometers in thickness.

2. A porous support surface bearing a polymeric coating prepared according to a method of forming a polymeric coating on a support surface, the method comprising:
    a) providing a porous support surface;
    b) providing a nonpolymeric grafting reagent comprising at least two photoinitiator groups, at least one of which to be activated in order to covalently attach the grafting reagent to the surface itself, and further comprising one or more substituents comprising positively charged groups;
    c) providing at least one polymerizable monomer solution to be contacted with the surface, in the presence of the grafting reagent, and to be polymerized upon activation of the grafting reagent; and
    d) applying the grafting reagent and monomer solution to the surface to coat the surface with the grafting reagent and to cause the polymerization of monomers to the surface upon activation of the grafting reagent and the covalent attachment of the reagent to the surface, wherein the polymeric coating is less than about 100 nanometers in thickness.

3. A porous surface according to claim 2 wherein the support surface comprises a material selected from the group consisting of polyolefins, polystyrenes, poly(alkyl)methacrylates and poly(alkyl) acrylates, polyacrylonitriles, poly(vinylacetates), poly(vinyl alcohols), chlorine-containing polymers such as poly(vinyl) chloride, polyoxymethylenes, polycarbonates, polyamides, polyimides, polyurethanes, polyvinylidene difluoride (PVDF), phenolics, amino-epoxy resins, polyesters, silicones, polyethylene terephthalates (PET), polyglycolic acids (PGA), poly-(p-phenyleneterephthalamides), polyphosphazenes, polypropylenes, parylenes, silanes, and silicone elastomers, as well as copolymers and combinations thereof, and the grafting reagent is selected from:
    ethylenebis(4-benzoylbenzyldimethylammonium) dibromide (Diphoto-Diquat); hexamethylenebis(4-benzoylbenzyldimethylammonium) dibromide (Diphoto-Diquat); 1,4-bis(4-benzoylbenzyl)-1,4-dimethylpiperazinediium dibromide (Diphoto-Diquat); bis(4-benzoylbenzyl)hexamethylenetetraminediium dibromide (Diphoto-Diquat): bis[2-(4-benzoylbenzyldimethylammonio)ethyl]-4-benzoylbenzylmethylammonium tribromide (Triphoto-Triquat): 4,4-bis(4-benzoylbenzyl)morpholinium bromide (Diphoto-Monoquat); ethylenebis[(2-(4-benzoylbenzyldimethylammonio)ethyl)-4-benzoylbenzylmethylammonium]tetrabromide (Tetraphoto-Tetraquat); and 1,1,4,4-tetrakis(4-benzoylbenzyl)piperazinediium Dibromide (Tetraphoto-Diquat) and analogues thereof, and wherein the polymer is formed by the polymerization of polymerizable monomers selected from:
    a) neutral hydrophilic structural monomers selected from acrylamide, methacrylamide, N-alkylacrylamides, N-vinylpyrrolidinone, N-vinylacetamide, N-vinyl formamide, hydroxyethylacrylate, hydroxyethylmethacrylate, hydroxypropyl acrylate or methacrylate, glycerolmonomethacrylate, and glycerolmonoacrylate;
    b) negatively charged hydrophilic functional monomers selected from acrylic acid, methacrylic acid, maleic acid, fumaric acid, itaconic acid, AMPS (acrylamidomethylpropane sulfonic acid), vinyl phosphoric acid, vinylbenzoic acid; and
    c) positively charged monomers selected from 3-aminopropylmethacrylamide (APMA), methacrylamidopropyltrimethylammonium chloride (MAPTAC), N,N-dimethylaminoethylmethacrylate, N,N-diethylaminoethylacrylate.

4. A device comprising a surface bearing a polymer coating formed according a method comprising the steps of:
    a) providing a support surface;
    b) providing a nonpolymeric grafting reagent comprising at least two photoinitiator groups, the grafting reagent having one or more substituents comprising positively charged groups;

c) providing at least one polymerizable monomer solution to be contacted with the surface, in the presence of the grafting reagent, and to be polymerized upon activation of the photoinitiator; and d) applying the grafting reagent and monomer solution to the surface to coat the surface with the grafting reagent and to cause the polymerization of monomers to the surface upon activation of the grafting reagent, wherein the support surface comprises a porous support surface and the polymer coating is covalently attached to the surface by the residues of one or more latent reactive groups provided by the grafting reagent and the polymer coating is less than about 100 nanometers in thickness.

5. A device comprising a surface bearing a polymer coating, the polymer coating being formed by a method comprising the steps of:

a) providing a porous support surface;

b) providing a nonpolymeric grafting reagent comprising at least two photoinitiator groups, at least one of which is to be activated in order to covalently attach the grafting reagent to the surface itself, and further comprising one or more substituents comprising positively charged groups;

c) providing at least one polymerizable monomer solution to be contacted with the surface, in the presence of the grafting reagent, and to be polymerized upon activation of the grafting reagent; and d) applying the grafting reagent and monomer solution to the surface to coat the surface with the grafting reagent and to cause the polymerization of monomers to the surface upon activation of the grafting reagent and the covalent attachment of the reagent to the surface, wherein the polymer coating is less than about 100 nanometers in thickness, and further wherein the support surface comprises a material selected from the group consisting of polyolefins, polystyrenes, poly(alkyl)methacrylates and poly(alkyl) acrylates, polyacrylonitriles, poly(vinylacetates), poly(vinyl alcohols), chlorine-containing polymers such as poly(vinyl) chloride, polyoxymethylenes, polycarbonates, polyamides, polyimides, polyurethanes, polyvinylidene difluoride (PVDF), phenolics, amino-epoxy resins, polyesters, silicones, polyethylene terephthalates (PET), polyglycolic acids (PGA), poly-(p-phenyleneterephthalamides), polyphosphazenes, polypropylenes, parylenes, silanes, and silicone elastomers, as well as copolymers and combinations thereof, and the grafting reagent is selected from:

ethylenebis(4-benzoylbenzyldimethylammonium) dibromide (Diphoto-Diquat); hexamethylenebis(4-benzoylbenzyldimethylammonium) dibromide (Diphoto-Diquat); 1,4-bis(4-benzoylbenzyl)-1,4-dimethylpiperazinediium dibromide (Diphoto-Diquat); bis(4-benzoylbenzyl)hexamethylenetetraminediium dibromide (Diphoto-Diquat): bis[2-(4-benzoylbenzyldimethylammonio)ethyl]-4-benzoylbenzylmethylammonium tribromide (Triphoto-Triquat): 4,4-bis(4-benzoylbenzyl)morpholinium bromide (Diphoto-Monoquat); ethylenebis[(2-(4-benzoylbenzyldimethylammonio)ethyl)-4-benzoylbenzylmethylammonium]tetrabromide (Tetraphoto-Tetraquat); and 1,1,4,4-tetrakis(4-benzoylbenzyl)piperazinediium Dibromide (Tetraphoto-Diquat), and analogues thereof, and wherein the polymer is formed by the polymerization of polymerizable monomers selected from:

a) neutral hydrophilic structural monomers selected from acrylamide, methacrylamide, N-alkylacrylamides, N-vinylpyrrolidinone, N-vinylacetamide, N-vinyl formamide, hydroxyethylacrylate, hydroxyethylmethacrylate, hydroxypropyl acrylate or methacrylate, glycerolmonomethacrylate, and glycerolmonoacrylate;

b) negatively charged hydrophilic functional monomers selected from acrylic acid, methacrylic acid, maleic acid, fumaric acid, itaconic acid, AMPS (acrylamidomethylpropane sulfonic acid), vinyl phosphoric acid, vinylbenzoic acid; and c) positively charged monomers selected from 3-aminopropylmethacrylamide (APMA), methacrylamidopropyltrimethylammonium chloride (MAPTAC), N,N-dimethylaminoethylmethacrylate, N,N-diethylaminoethylacrylate, and combinations thereof.

6. A device comprising a surface bearing a polymer coating formed according a method comprising the steps of:

a) providing a support surface;

b) providing a nonpolymeric grafting reagent comprising at least two photoinitiator groups, the grafting reagent having one or more substituents comprising positively charged groups;

c) providing at least one polymerizable monomer solution to be contacted with the surface, in the presence of the grafting reagent, and to be polymerized upon activation of the photoinitiator; and d) applying the grafting reagent and monomer solution to the surface to coat the surface with the grafting reagent and to cause the polymerization of monomers to the surface upon activation of the grafting reagent, wherein the support surface comprises a porous support surface and the polymer coating is covalently attached to the surface and the polymer coating is less than about 100 nanometers in thickness.

7. A support surface bearing a polymeric coating prepared according to a method comprising the steps of:

a) providing a support surface;

b) providing a nonpolymeric grafting reagent comprising four photoinitiator groups, the grafting reagent having a nonpolymeric core molecule with the four photoinitiator groups attached to the core molecule;

c) providing at least one polymerizable monomer to be contacted with the surface, in the presence of the grafting reagent, and to be polymerized upon activation of at least one of the photoinitiator groups; and d) applying the grafting reagent and monomer solution to the surface to coat the surface with the grafting reagent and to cause the polymerization of monomers to the surface upon activation of the grafting reagent, wherein the support surface comprises a porous support surface and the polymeric coating is less than about 100 nanometers in thickness, and the polymeric coating is covalently attached to the surface.

8. A porous surface according to claim 7 wherein the support surface comprises a material selected from the group consisting of polyolefins, polystyrenes, poly(alkyl)methacrylates and poly(alkyl) acrylates, polyacrylonitriles, poly(vinylacetates), poly(vinyl alcohols), chlorine-containing polymers such as poly(vinyl) chloride, polyoxymethylenes, polycarbonates, polyamides, polyimides, polyurethanes, polyvinylidene difluoride (PVDF), phenolics, amino-epoxy resins, polyesters, silicones, polyethylene terephthalates (PET), polyglycolic acids (PGA), poly-(p-phenyleneterephthalamides), polyphosphazenes, polypropylenes, parylenes, silanes, and silicone elastomers, as well as copolymers and combinations thereof, and the grafting reagent is selected from:

tetrakis (4-benzoylbenzyl ether), the tetrakis (4-benzoylbenzoate ester) of pentaerythritol, and an acylated derivative of tetraphenylmethane, and wherein the polymer is formed by the polymerization of polymerizable monomers selected from:

a) neutral hydrophilic structural monomers selected from acrylamide, methacrylamide, N-alkylacrylamides, N-vinylpyrrolidinone, N-vinylacetamide, N-vinyl formamide, hydroxyethylacrylate, hydroxyethylmethacrylate, hydroxypropyl acrylate or methacrylate, glycerolmonomethacrylate, and glycerolmonoacrylate;

b) negatively charged hydrophilic functional monomers selected from acrylic acid, methacrylic acid, maleic acid, fumaric acid, itaconic acid, AMPS (acrylamidomethyipropane sulfonic acid), vinyl phosphoric acid, vinylbenzoic acid;

c) positively charged monomers selected from 3-aminopropylmethacrylamide (APMA), methacrylamidopropyltrimethylammonium chloride (MAPTAC), N,N-dimethylaminoethylmethacrylate, N,N-diethylaminoethylacrylate; and d) macromeric polymerizable molecule selected from poly(ethylene glycol)monomethyacrylate, methoxypoly(ethylene glycol)monomethacrylate, poly(ethylene glycol)monoacrylate, methyacrylamidopoly(acrylamide), poly(acrylamide-co-3-methacrylamidopropylacrylamide), poly(vinylalcohol)methacrylate, poly(vinylalcohol)acrylate, poly(vinylalcohol)dimethacrylate, and combinations thereof.

* * * * *